United States Patent
Kuhn et al.

(10) Patent No.: US 10,471,216 B2
(45) Date of Patent: Nov. 12, 2019

(54) APPARATUS AND METHOD FOR RECORDING THE AMOUNT OF MEDICAMENT EJECTED FROM AN INJECTION DEVICE

(71) Applicant: SANOFI-AVENTIS DEUTSCHLAND GMBH, Frankfurt am Main (DE)

(72) Inventors: Bernd Kuhn, Frankfurt am Main (DE); Michael Schabbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 693 days.

(21) Appl. No.: 14/902,806

(22) PCT Filed: Jul. 3, 2014

(86) PCT No.: PCT/EP2014/064155
§ 371 (c)(1),
(2) Date: Jan. 4, 2016

(87) PCT Pub. No.: WO2015/001008
PCT Pub. Date: Jan. 8, 2015

(65) Prior Publication Data
US 2016/0235925 A1    Aug. 18, 2016

(30) Foreign Application Priority Data
Jul. 5, 2013    (EP) .................................... 13175219

(51) Int. Cl.
*A61M 5/315* (2006.01)
*A61M 5/24* (2006.01)
*A61M 5/31* (2006.01)

(52) U.S. Cl.
CPC .......... *A61M 5/31568* (2013.01); *A61M 5/24* (2013.01); *A61M 5/31525* (2013.01);
(Continued)

(58) Field of Classification Search
CPC . A61M 5/31568; A61M 5/24; A61M 5/31525
See application file for complete search history.

(56) References Cited

U.S. PATENT DOCUMENTS 6,277,099 B1 *   8/2001   Strowe .............. A61M 5/31553
                                                        604/186
2012/0283648 A1   11/2012   Veasey et al.

FOREIGN PATENT DOCUMENTS

| CN | 101405738 | 4/2009 |
|----|-----------|--------|
| CN | 102458514 | 5/2012 |

(Continued)

OTHER PUBLICATIONS

International Preliminary Report on Patentability in International Application No. PCT/EP2014/064155, dated Jan. 5, 2016, 6 pages.

(Continued)

*Primary Examiner* — Edelmira Bosques
(74) *Attorney, Agent, or Firm* — Fish & Richardson P.C.

(57) ABSTRACT

An apparatus for recording the amount of medicament ejected from an injection device includes a processor to receive information from a primary sensor and a secondary sensor and a memory. The primary sensor is configured to detect information displayed or generated by said injection device and to generate output corresponding thereto. The secondary sensor is configured to detect ejection of medicament from said injection device. The processor is configured to process the output generated by the primary sensor and to record in the memory information indicative of an amount of medicament ejected from said injection device only when the processor determines, on the basis of information received from the secondary sensor, that more than a predetermined amount of medicament has been ejected.

22 Claims, 3 Drawing Sheets

(52) U.S. Cl.
CPC .............. *A61M 2005/3126* (2013.01); *A61M 2205/3306* (2013.01); *A61M 2205/3375* (2013.01); *A61M 2205/52* (2013.01)

(56) References Cited

FOREIGN PATENT DOCUMENTS

| | | |
|---|---|---|
| CN | 202236677 | 5/2012 |
| CN | 102905613 | 1/2013 |
| WO | WO 2007/107564 | 9/2007 |
| WO | WO 2010/142598 | 12/2010 |
| WO | WO 2011/117212 | 9/2011 |
| WO | WO 2013/120777 | 8/2013 |

OTHER PUBLICATIONS

International Search Report and Written Opinion in International Application No. PCT/EP2014/064155, dated Aug. 7, 2014, 8 pages.

* cited by examiner

APPARATUS AND METHOD FOR RECORDING THE AMOUNT OF MEDICAMENT EJECTED FROM AN INJECTION DEVICE

CROSS-REFERENCE TO RELATED APPLICATIONS

This application is a U.S. national stage application under 35 USC § 371 of International Application No. PCT/EP2014/064155, filed on Jul. 3, 2014, which claims priority to European Patent Application No. 13175219.8, filed on Jul. 5, 2013, the entire contents of which are incorporated herein by reference.

TECHNICAL FIELD

The present disclosure relates to an apparatus and method for recording the amount of medicament ejected from an injection device.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses which are administered. Supplemental devices may be used to record dose history information such as the various times at which insulin is administered and the quantity of insulin administered at each such time.

Although electronically recording dose history information addresses the problem of inaccurately recording such information manually, it has the disadvantage of providing a false representation of how much medicament a patient actually injects themselves with. In particular, before administering an injection a patient may eject a small amount of medicament in a so-called prime shot to remove air from within their needle. Supplemental devices configured to record how much medicament is ejected from an injection device will record both amounts of medicament ejected during prime shots in addition to amounts of medicament that are actually injected into a patient. It will thus be appreciated that simply recording how much medicament is ejected from an injection device does not give an accurate determination of how much medicament is actually injected into a patient. Not knowing such information within an acceptable degree of tolerance may have potentially serious consequences if a patient is subsequently over or under prescribed medication on the basis of an incorrect understanding of how much medicament has previously been injected.

SUMMARY

According to a first aspect of the invention there is provided apparatus for recording the amount of medicament ejected from an injection device, the apparatus comprising:
a processor coupled to receive information from a primary sensor and a secondary sensor; and
a memory, wherein:

the primary sensor is configured to detect information displayed or generated by said injection device and to generate output corresponding thereto,
the secondary sensor is configured to detect ejection of medicament from said injection device, and
the processor is configured to process the output generated by the primary sensor and to record in the memory information indicative of an amount of medicament ejected from said injection device only when the processor determines, on the basis of information received from the secondary sensor, that more than a predetermined amount of medicament has been ejected.

This can provide that information associated with a prime shot (i.e. when less than the predetermined amount of medicament is ejected) is not recorded in the memory. In particular, information indicative of an amount of medicament ejected during such a prime shot can be prevented from being recorded in the memory without requiring any further action to be taken by a user. This addresses the disadvantage associated with previously proposed supplemental devices which record the total amount medicament ejected from an injection device. In particular, by not recording information associated with prime shots, the information stored in the memory gives a more accurate representation of the total amount of medicament which has actually been injected into a patient. It will be appreciated that by improving the quality of such recorded information in this manner, this will reduce the likelihood of a patient being over or under prescribed medication when the patient's prescription requires an understanding of how much medicament with which they have previously been injected.

The secondary sensor may be configured to sense the position of a part of said injection device which moves while medicament is ejected from said injection device, and to provide information corresponding to said position to the processor; and the processor may be configured to process the output generated by the primary sensor, and to record in the memory information indicative of an amount of medicament ejected from said injection device, when said part is determined by the processor to have moved more than a threshold distance.

Since the processor can continually monitor the position of said part, the processor can easily determine when an injection is taking place i.e. when said part is determined to have moved more than the threshold distance. If said part is determined not to have moved more than the threshold distance during an injection, then the processor can make a determination that a prime shot occurred. It will be appreciated that different users may eject different amounts during prime shots. The predetermined distance may thus be configured depending on the extent of movement of said part which is expected during a prime shot. For instance, the predetermined distance may be manually configurable by a user or it may be pre-set during manufacture.

The secondary sensor may be configured to sense the position of a part of said injection device which moves while medicament is ejected from said injection device, and to provide a signal to the processor indicating that said part has moved more than a threshold distance when such an event is detected to have occurred; and the processor may be configured to process the output generated by the primary sensor, and to record in the memory information indicative of an amount of medicament ejected from said injection device, upon receipt of said signal from the secondary sensor.

The secondary sensor may have a level of sensitivity such that small movements of said monitored part go unnoticed.

For instance the secondary sensor may be configured such that movements of said part during a prime shot go unnoticed. Information indicative of dose amounts ejected during prime shots will thus not be recorded in the memory.

The part of said injection device may be a last-dose nut. The part of said injection device may be a pen lead screw. The part of said injection device may be a bearing. These examples of what the part of said injection device may embody are merely exemplary. It will be appreciated that said part may comprise any part of an injection device which moves only when medicament is ejected therefrom.

The apparatus can thus be used with some types of injection devices that are already available on the market.

The secondary sensor may be an optical sensor. The secondary sensor may be an acoustic sensor. The secondary sensor may be a metal detector. The secondary sensor may be any other type of sensor which is suitable for monitoring the position of the chosen part of said injection device to be monitored.

The secondary sensor may be an optical sensor and said part may be a last-dose nut which is visible through a window provided on said injection device.

The apparatus and said injection device may be coupled to one another. This provides that a user may use an injection device in a manner which they normally would, whilst benefiting from the functionality of the apparatus.

The apparatus and said injection device may be integral.

According to a second aspect of the invention there is provided a method comprising:

a primary sensor detecting information displayed or generated by an injection device and generating output corresponding thereto, a secondary sensor detecting ejection of medicament from said injection device, a processor determining, on the basis of information received from the secondary sensor, that more than a predetermined amount of medicament has been ejected from said injection device, and only when the processor determines that more than the predetermined amount of medicament has been ejected, the processor processing the output generated by the primary sensor and recording in a memory information indicative of an amount of medicament ejected from said injection device.

This can provide that information associated with a prime shot (i.e. when less than the predetermined amount of medicament is ejected) is not recorded in the memory. In particular, information indicative of an amount of medicament ejected during such a prime shot is not recorded in the memory without any further action.

The method may further comprise: the secondary sensor sensing the position of a part of said injection device which moves while medicament is ejected from said injection device, and providing information corresponding to said position to the processor; and the processor processing the output generated by the primary sensor, and recording in the memory information indicative of an amount of medicament ejected from said injection device, when said part is determined by the processor to have moved more than a threshold distance.

The method may further comprise: the secondary sensor sensing the position of a part of said injection device which moves while medicament is ejected from said injection device, and providing a signal to the processor indicating that said part has moved more than a threshold distance when such an event is detected to have occurred; and the processor processing the output generated by the primary sensor, and recording in the memory information indicative of an amount of medicament ejected from said injection device, upon receipt of said signal from the secondary sensor.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
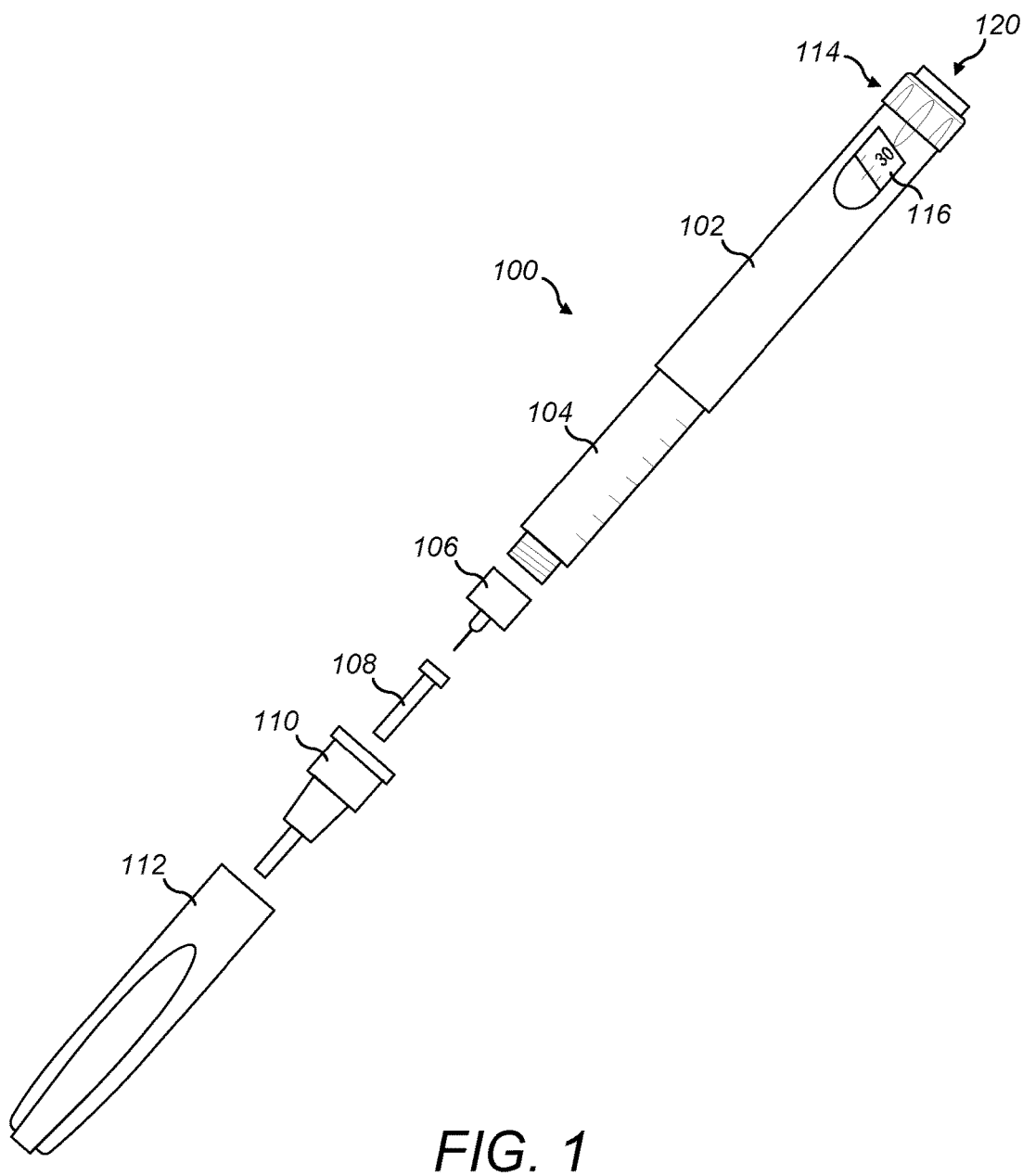
FIG. 1 is an exploded view of a prior art injection device 100.

FIG. 1 is an exploded view of an injection device 100, which may for instance represent Sanofi's Solostar™ (R) insulin injection pen.

The injection device 100 is a pre-filled, disposable injection pen that comprises a housing 102 and contains an insulin container 104, to which a needle 106 can be affixed. The needle is protected by an inner needle cap 108 and an outer needle cap 110, which in turn can be covered by a cap 112. An insulin dose to be ejected from injection device 100 can be selected by turning the dosage knob 114, and the selected dose is then displayed via dosage window 116, for instance in multiples of so-called International Units (IU), wherein one IU is the biological equivalent of about 45.5 micrograms of pure crystalline insulin (1/22 mg). An example of a selected dose displayed in dosage window 116 may be 30 IUs, as shown in FIG. 1. It should be noted that the selected dose may equally well be displayed differently, for instance by means of an electronic display.

Turning the dosage knob 114 causes a mechanical click sound to provide acoustic feedback to a user. The numbers displayed in dosage window 116 are printed on a sleeve 118 (see FIG. 4) that is contained in housing 102 and mechanically interacts with a piston within the insulin container 104. When needle 106 is stuck into a skin portion of a patient, and then injection button 120 is pushed, the insulin dose displayed in display window 116 is ejected from injection device 100. When the needle 106 of injection device 100 remains for a certain time in the skin portion after the injection button 120 is pushed, a high percentage of the dose is actually injected into the patient's body. Ejection of the insulin dose also causes a mechanical click sound, which is however different from the sounds produced when using dosage knob 114.

Injection device 100 may be used for several injection processes until either insulin container 104 is empty or the expiration date of injection device 100 (e.g. 28 days after the first use) is reached.

Furthermore, before using injection device 100 for the first time, it may be necessary to perform a so-called prime shot to remove air from insulin container 104 and needle 106. This may be achieved by selecting 2 IUs of insulin and pressing injection button 120 while holding injection device 100 with the needle 106 pointing upwards.

Figure 2:
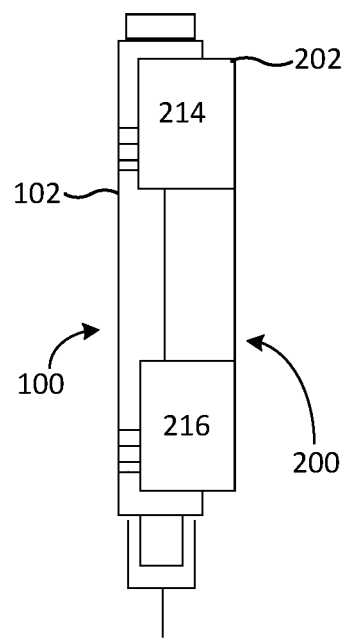
FIG. 2 illustrates a supplemental device 200 according to an aspect of the present invention while in use.

With reference to FIG. 2, a supplemental device 200 may be releasably attached to an injection device 100 (such as the one heretofore described) for the purpose of recording information related to a condition and/or use of the injection device 100. In particular, the supplemental device 200 may be used to record and store dose history information (for example when particular injections occurred and how much insulin was ejected during each such injection) in an internal memory.

Figure 3:
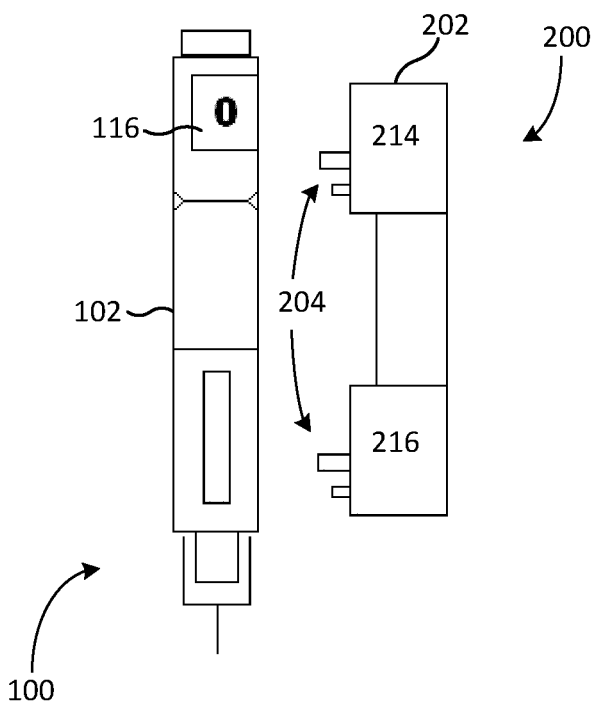
FIG. 3 illustrates a supplemental device 200 prior to being coupled to an injection device 100.

FIG. 3 illustrates the supplemental device 200 when it is detached from an injection device 100. The supplemental device 200 comprises a housing 202 which is provided with a mating unit 204 for embracing the housing 102 of the injection device 100. In particular the mating unit may be configured to snap-fit onto the housing 102 of an injection device 100 in such a way that the device 200 can be subsequently removed therefrom. The mating unit 204 need not however be of the snap-fit variety and other arrangements that are suitable for coupling the supplemental device 200 to an injection device 100 may be used instead, such as a strap.

The supplemental device 200 is provided with a plurality of sensors for gathering information from the injection device 100. Information gathered from the injection device 100, or dose history information determined therefrom, can be stored in an internal memory of the supplemental device 200. An example of a suitable type of sensor is an optical sensor which may be used to gather information displayed in the dosage window 116 of an injection device 100. A supplemental device 200 having such an optical sensor is caused to obstruct the dosage window 116 of an injection device 100 when coupled thereto as illustrated in FIGS. 2 & 4.

Another example of a suitable sensor which may be used to gather information from an injection device 100 is an acoustic sensor. It will be appreciated that various combinations of the same or different kinds of sensors may be used for this purpose.

Figure 4:
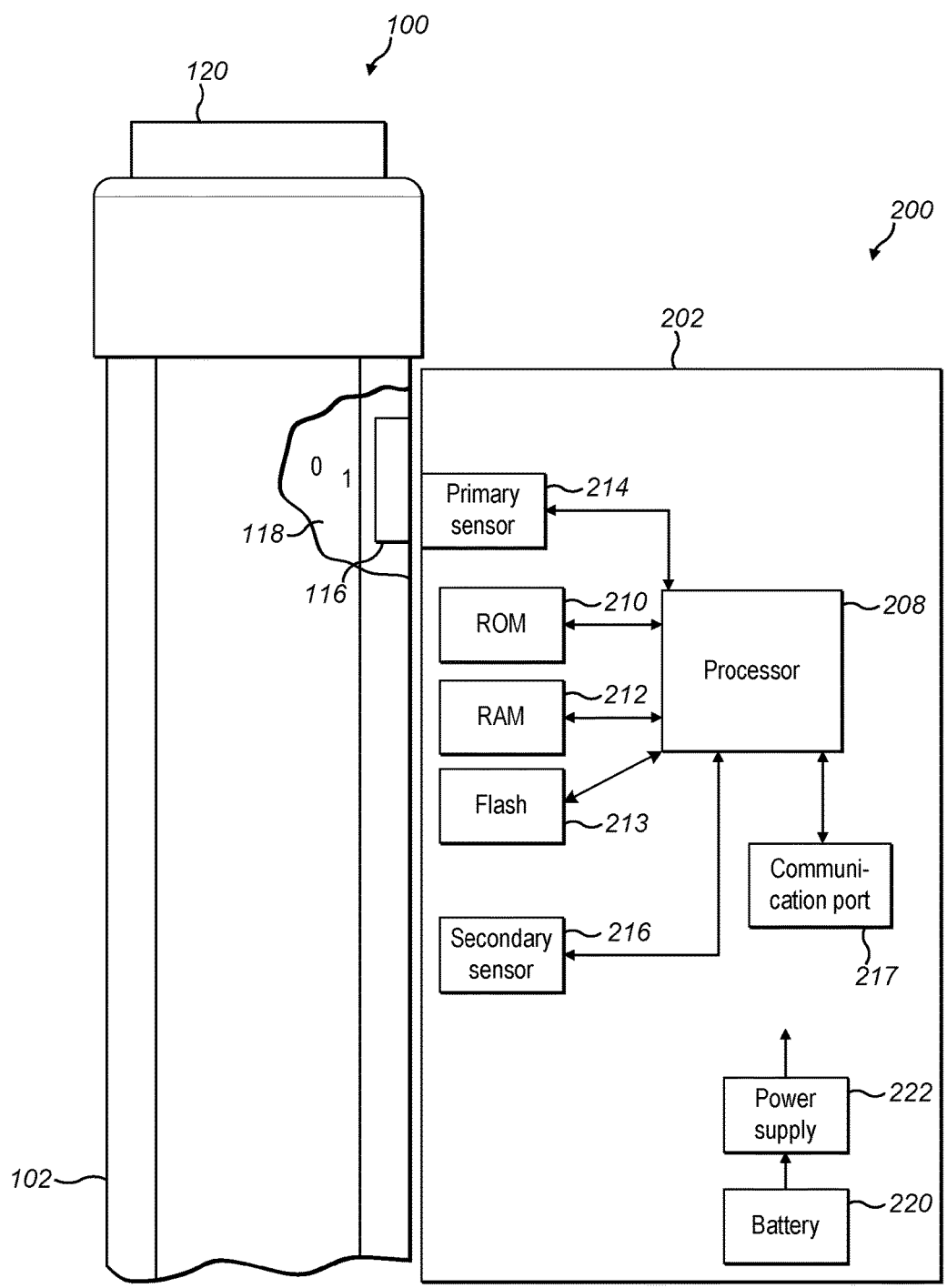
FIG. 4 is an internal schematic view of a supplemental device 200 coupled to an injection device 100.

FIG. 4 illustrates an internal schematic view of a supplemental device 200 in a state where it is coupled to an injection device 100. Within the housing 202 of the supplemental device 200, a variety of components are located. These are controlled by a processor 208 which may for instance be a microprocessor, a Digital Signal Processor (DSP), Application Specific Integrated Circuit (ASIC), Field Programmable Gate Array (FPGA) or the like.

The supplemental device 200 comprises a non-volatile memory such as a ROM 210, a volatile memory such as a RAM 212 and a writable non-volatile memory such as a flash memory 213. The ROM 210 may be configured to store software and/or firmware. This software/firmware may control operations of the processor 208. The processor 208 utilises RAM 212 to execute the software/firmware stored in the ROM 210. The processor 208 utilises the flash memory 213 to store dose history information.

The supplemental device 200 is provided with a primary sensor 214. Information collected by the primary sensor 214 may be used by the processor 208 to determine how much insulin is ejected from an injection device 100 during an injection (not during a prime shot as will be explained below).

In one example the primary sensor 214 may be an optical sensor for reading information provided on the sleeve 118 of an injection device 100 through the dosage window 116 (see FIG. 4). Such information may comprise numbers or other markings located on the sleeve 118 which indicate an amount of dose which has been dialed or is yet to be dispensed. More specifically the optical sensor may comprise an Optical Character Recognition (OCR) reader that is capable of capturing images of the dosage window 116 in which a currently selected dose is displayed. Such an OCR reader may be further capable of recognizing characters (e.g. numbers) from the captured image and configured to provide this information to processor 208. Alternatively however, the optical sensor may be configured to merely capture images and provide information corresponding to such images to the processor 208. In such an arrangement the optical sensor may be a camera and the processor 208 may be configured to perform the aforementioned OCR on the captured images.

The above mentioned OCR reader may constitute a dose dialed detector operable to detect a dose of medicament dialed. The OCR reader may also constitute a dose delivery determiner for determining that a dose of medicament has been delivered. The OCR reader and the processor 208 may together constitute a quantity determiner for determining a quantity of medicament that has been delivered (and/or is yet to be delivered, if any, by comparing an amount of dose dialed with that delivered). The processor 208 provides a function of a clock configured to determine a current time.

In another example the primary sensor 214 may alternatively comprise an acoustic sensor for detecting sounds produced by an injection device 100. The processor 208 may be configured to control and/or receive signals from such an acoustic sensor. Sounds may for instance occur when a dose is ejected from an injection device 100 by pressing injection button 120. It will thus be appreciated that by analysing information collected by an acoustic sensor the processor 208 will be able to determine an amount of insulin ejected during an injection.

Referring again to FIG. 4, the supplemental device 200 is further provided with a secondary sensor 216. Information collected from the secondary sensor 216 may be used by the processor 208 to determine when insulin is being injected into a patient from within an injection device 100. Only when insulin is detected as being injected (i.e. upon determination by the processor 208, on the basis of output from the secondary sensor 216, that more than a threshold amount of insulin has been ejected) is information gathered by the primary sensor 214 processed to determine dose history information and subsequently recorded for example in the flash memory 213. In other words, dose history information determined on the basis of output from the primary sensor 214 is only recorded when the processor determines, on the basis of output from the secondary sensor 216, that more than a threshold amount of insulin has been ejected from an injection device 100.

The secondary sensor 216 may be configured such that when the supplemental device 200 is coupled to an injection device 100, the secondary sensor 216 can sense the position of a part of the injection device 100 which only moves when insulin is being ejected. Information collected by the secondary sensor 216 can thus be analysed by the processor 208 to determine when such part is moving, thereby enabling the processor 208 to determine when insulin is actually being injected.

Some examples of injection device parts which the secondary sensor 216 may be configured to sense the movement of include the pen lead screw, bearing or last-dose nut. For example, if a supplemental device 200 were to track the movement of part of a drug delivery device having the drive mechanism described in US2012/0283648, the secondary sensor 216 may be configured to sense the position of the last-dose nut (denoted as item 21). Since last-dose nuts move linearly inside drug delivery devices within which they are provided when medicament is caused to be ejected, secondary sensors 216 which detect the movement of last-dose nuts may be referred to as linear movement detectors or pole impulse detectors.

Since the last-dose nut within a Solostar™ type injection device is close to the device's outer surface, there are a variety of ways in which to sense its position. For instance a secondary sensor 216 used to sense the position of such a last-dose nut may comprise an acoustic sensor (such as an ultrasound sensor or a sonar detector). Alternatively, if the last-dose nut is formed of metal (or metal compounds) the secondary sensor 216 may comprise a metal detector, thereby allowing for electromagnetic determination of such a last-dose nut's position. Furthermore, the injection device 100 may be provided with a window through which the last-dose nut is visible, thereby enabling the secondary sensor 216 to comprise an optical sensor.

Last-dose nuts are arranged to progressively move along the length of an injection device as the amount of medicament to be ejected is exhausted. In other words when medicament is ejected from within a cartridge, the last-dose nut of an injection device used to eject such medicament will progressively move along the length of the injection device as medicament is being ejected. In the particular case of a Solostar™ type injection device, the last-dose nut will move along the length of the injection device 100 as a medicament cartridge within the device 100 is progressively exhausted.

An injection device 100 may be configured such that when less than a predetermined amount of insulin is ejected, the last-dose nut shifts less than a threshold amount.

In some embodiments the secondary sensor 216 that is configured to sense the position of such a last-dose nut may be a high-resolution sensor, capable of continuously monitoring the last-dose nut's position. The processor 208 receives output from the secondary sensor 216, and determines that an injection is taking place when the position of the last-dose nut is determined by the processor 208 to have moved more than the aforementioned threshold distance in a particular time frame. It will be appreciated that when the last-dose nut is caused to move the threshold distance, a predetermined amount of medicament is ejected from the injection device 100. Thus when the last-dose nut is caused to move more than the threshold distance, more than the predetermined amount of medicament is ejected from the injection device 100.

In the above example, if the last-dose nut is determined by the processor 208 to have shifted less than the threshold distance within the specified time frame (i.e. upon ejection of less than the predetermined amount of insulin) then that particular ejection will be regarded as a prime shot, and dose history information relating to that injection will not be recorded. However, if the last dose nut is determined by the processor 208 to have shifted at least the threshold distance within the specified time frame (i.e. upon ejection of at least the predetermined amount of insulin) then that particular ejection will be regarded as an injection, and dose history information relating to that injection will be recorded.

More specifically, the processor 208 in the above example may determine an injection as taking place when the last-dose nut is determined, on the basis of information output from the secondary sensor 216, to have moved at least 4 mm (or other predetermined distance) inside a specified time frame such as half a second (or another specified time frame). Advantageously, this enables insulin ejected during a prime shot (in this example, a prime shot which causes the last dose nut to move less than 4 mm) to be excluded from dose history information without any further action. If at least a predetermined amount of insulin is ejected inside the specified time frame (in this example, if the last-dose nut is caused to move at least 4 mm in less than half a second) then the processor 208 will determine, on the basis of output from the secondary sensor 216, that an injection is taking place (i.e. that insulin is being injected into a patient) and will start processing information output from the primary sensor 214 to determine dose history information and subsequently record it in the flash memory for instance. In particular such dose history information may relate to how much medicament is injected into a patient during the particular detected injection and the time of the injection.

The supplemental device 200 also has a battery 220 (see FIG. 4) which powers the processor 208 and other components of the supplemental device 200 by way of a power supply 222.

The supplemental device 200 may be used to transmit dose history information of a patient to a remote device (for example a computer or mobile device such as a smartphone) where such information may be stored. In such an embodiment the supplemental device 200 is provided with a communication port 217. Such a communication port 217 may comprise one of many components familiar to persons skilled in the art for transferring information between electronic devices (in this case the supplemental device 200 and another electronic device). For instance the communication port 217 may comprise, inter alia, a USB-port, a wireless unit such as a transceiver or an optical fibre connection port.

It will be appreciated that the above described embodiments are purely illustrative and are not limiting on the scope of the invention. Other variations and modifications will be apparent to persons skilled in the art upon reading the present application.

In some embodiments the secondary sensor 216 may be configured such that the last-dose nut of an injection device 100 shifts a distance below the limits of detection of the secondary sensor 216, when less than a predetermined amount of insulin is ejected. For example a secondary sensor 216 may not be able to detect movements less than a threshold distance of say 4 mm. In such embodiments, a prime shot which causes the last-dose nut (or any other monitored part of an injection device) to move a distance less than the threshold distance will go undetected. Advantageously this enables insulin ejected during such a non-detectable prime shot to be excluded from dose history information without any further action. However if a detectable amount of insulin is ejected (in this example, if the last-dose nut is caused to move at least 4 mm during an injection) the processor 208 will determine, on the basis of a signal output from the secondary sensor 216 in response to detected movement of the last dose nut, that an injection is taking place (i.e. that insulin is being injected into a patient). The processor will then start processing information output from the primary sensor 214 to determine dose history information and subsequently record it in the flash memory 213 for instance. Such dose history information may relate to how much medicament is injected into a patient during the particular detected injection and the time at which the injection took place.

Examples heretofore described which concern monitoring the position of a last-dose nut equally apply to instances in which any other part of an injection device other than a last-dose nut is monitored, provided such monitored part only moves when medicament is ejected from the injection device.

In some embodiments the supplemental device 200 and the injection device 100 may be releasably attachable to one another (for example, by means of a releasable snap-fit mechanism). In other embodiments they may be fixably attachable to one another (for example, by means of a non-releasable snap-fit mechanism or by means of an adhesive coupling). In other embodiments an apparatus may comprise the functionality of both the supplemental device 200 and an injection device 100. In other words the functionality of both the supplemental device 200 and an injection device 100 may be integrated in the same apparatus. In such an apparatus the part which embodies the functionality of the supplemental device 200 may be integral with the part that embodies the functionality of the injection device 100.

As aforementioned, in some embodiments the secondary sensor 216 is configured to sense the position of a part of an injection device 100 that moves only when medicament is being ejected (e.g. a last-dose nut). The secondary sensor 216 may be a high-resolution sensor, capable of continuously monitoring the part's position. The processor 208 receives output from the secondary sensor 216, indicative of the position of the part being monitored, and determines that an injection is taking place when its position is determined by the processor 208 to have moved more than a threshold distance within a particular time frame. In other embodiments however, the secondary sensor 216 may configured to determine when a part of an injection device 100 being monitored (e.g. a last-dose nut) moves a threshold distance within a predetermined amount of time. When this is determined by the secondary sensor 216 to have occurred the secondary sensor 216 outputs a signal to the processor 208. Upon receipt of this signal by the processor 208, the processor determines that an injection is taking place and starts processing information generated by the primary sensor 214.

The scope of the present invention is not limited to supplemental devices having an optical sensor or an acoustic sensor for detecting information related to one or more conditions and/or usages of an injection device. The scope of the present invention instead extends to include supplemental devices which are provided with any suitable sensor, or combination of sensors, for detecting information related to one or more conditions and/or usages of an injection device. Furthermore, although aspects of the present invention have been described in connection with an injection device configured to eject insulin, the scope of the present invention extends to include supplemental devices for use with any kind of injection device, regardless of what kind of medicament they are configured to eject. In particular supplemental devices according to aspects of the present invention can be used with injection devices configured to eject medicaments other than insulin.

Finally, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus for recording an amount of medicament ejected from an injection device, the apparatus comprising: a primary sensor arranged to detect dose information generated by the injection device, the primary sensor being configured to generate output corresponding to the detected dose information; a secondary sensor arranged to detect ejection of medicament from the injection device; a processor to receive information from the primary sensor and the secondary sensor; and a memory, wherein:

the processor is configured to process the output generated by the primary sensor, and record, in the memory, information indicative of the amount of medicament ejected from the injection device only when the processor determines, on the basis of information received from the secondary sensor, that more than a predetermined amount of the medicament has been ejected.

2. The apparatus of claim 1, wherein: the secondary sensor is configured to sense a position of a part of the injection device which moves while the medicament is ejected from the injection device, and to provide information corresponding to the position to the processor; and the processor is configured to process the output generated by the primary sensor, and to record, in the memory, information indicative of the amount of medicament ejected from the injection device, when the part is determined by the processor to have moved more than a threshold distance.

3. The apparatus of claim 2, wherein the part of the injection device is a last-dose nut.

4. The apparatus of claim 2, wherein the part of the injection device is a lead screw.

5. The apparatus of claim 2, wherein the part of the injection device is a bearing.

6. The apparatus of claim 2, wherein the secondary sensor is an optical sensor and the part is a last-dose nut which is visible through a window of the injection device.

7. The apparatus of claim 1, wherein: the secondary sensor is configured to sense a position of a part of the injection device which moves while the medicament is ejected from the injection device, and to provide a signal to the processor indicating that the part has moved more than a threshold distance when such an event is detected to have occurred; and the processor is configured to process the output generated by the primary sensor, and to record, in the memory, the information indicative of the amount of medicament ejected from the injection device, upon receipt of the signal from the secondary sensor.

8. The apparatus of claim 1, wherein the secondary sensor is an optical sensor.

9. The apparatus of claim 1, wherein the secondary sensor is an acoustic sensor.

10. The apparatus of claim 1, wherein the secondary sensor is a metal detector.

11. The apparatus of claim 1, wherein the apparatus and the injection device are coupled to one another.

12. The apparatus of claim 1, wherein the apparatus and the injection device are integral.

13. A method comprising: positioning a primary sensor to detect information displayed or generated by an injection device and generate output corresponding thereto, positioning a secondary sensor to detect ejection of medicament from the injection device, determining, on the basis of detecting the ejection of the medicament, that more than a predetermined amount of the medicament has been ejected from the injection device, and after determining that more than the predetermined amount of the medicament has been ejected, processing the output corresponding to the information displayed or generated by the injection device and recording in a memory information indicative of an amount of medicament ejected, from the injection device.

14. The method of claim 13, comprising: sensing, using the secondary sensor, a position of a part of the injection device that moves while the medicament is ejected from the injection device; and, after determining that the part has moved more than a threshold distance based on the sensed position of the part of the injection device, processing the output corresponding to the information displayed or generated by the injection device and recording in the memory information indicative of the amount of the medicament ejected from the injection device.

15. The method of claim 13, comprising: sensing, using the secondary sensor, that a part of the injection device has moved more than a threshold distance; and then processing the output corresponding to the information displayed or generated by the injection device and recording in the memory information indicative of the amount of the medicament ejected from the injection device.

16. A method comprising: receiving, from a primary sensor positioned to detect information displayed or generated by an injection device, output indicative of information displayed or generated by the injection device; receiving, from a secondary sensor positioned to detect the ejection of medicament from the injection device, information generated in response to detecting the ejection of the medicament from the injection device; processing the output indicative of information displayed or generated by the injection device; and recording information indicative of an amount of the medicament ejected from the injection device only in response to determining, based on information generated in response to detecting ejection of the medicament from the injection device, that more than a predetermined amount of the medicament has been ejected.

17. The method of claim 16, comprising recording the information indicative of the amount of the medicament ejected from the injection device in response to determining a part of the injection device has moved more than a threshold distance, the part of the injection device being configured to move when the medicament is ejected from the injection device.

18. The method of claim 17, comprising receiving, from the secondary sensor for detecting the ejection of the medicament from the injection device, information corresponding to a position of the part of the injection device.

19. The method of claim 16, comprising: recording information indicative of the amount of the medicament ejected from the injection device upon receiving a signal indicating that a part of the injection device has moved more than a threshold distance, the part of the injection device being configured to move when the medicament is ejected from the injection device.

20. The method of claim 19, comprising: receiving, from the secondary sensor for detecting the ejection of the medicament from the injection device, the signal.

21. The method of claim 16, wherein recording the information indicative of the amount of the medicament ejected from the injection device comprises: recording information indicative of an amount of the medicament ejected from the injection device during a second ejection in which more than the predetermined amount of the medicament was ejected, without recording information indicative of an amount of the medicament ejected from the injection during a first ejection in which less than the predetermined amount of the medicament was ejected.

22. The method of claim 21, wherein the first ejection occurs before the second ejection and corresponds to a prime shot.

* * * * *